(12) United States Patent
Orlowski et al.

(10) Patent No.: US 7,335,691 B2
(45) Date of Patent: Feb. 26, 2008

(54) CARIES PREVENTIVE DESENSITIZING AND FLUORIDIZING DENTAL VARNISHES

(75) Inventors: Jan A. Orlowski, Alta Dena, CA (US); David V. Butler, West Covina, CA (US); Lindsay K. McKinley, Downey, CA (US)

(73) Assignees: Scientific Pharmaceuticals, Inc., Pomona, CA (US); Omnii Oral Pharmaceuticals, West Palm Beach, FL (US)

( * ) Notice: Subject to any disclaimer, the term of this patent is extended or adjusted under 35 U.S.C. 154(b) by 610 days.

(21) Appl. No.: 10/884,390

(22) Filed: Jul. 2, 2004

(65) Prior Publication Data

US 2006/0004120 A1 Jan. 5, 2006

(51) Int. Cl.
*A61P 35/00* (2006.01)
*A61K 6/08* (2006.01)
*C08K 3/34* (2006.01)

(52) U.S. Cl. .............. 524/270; 524/492; 523/105; 523/115

(58) Field of Classification Search .......... 523/115, 523/105; 524/270
See application file for complete search history.

(56) References Cited

U.S. PATENT DOCUMENTS

| | | | |
|---|---|---|---|
| 2,407,248 A | 9/1946 | Borglin | |
| 2,630,397 A | 3/1953 | Cowan et al. | |
| 2,788,287 A | 4/1957 | Zweig | |
| 3,081,227 A | 3/1963 | Wimberly | |
| 3,087,904 A | 4/1963 | Kalden | |
| 3,266,147 A | 8/1966 | Goldman | |
| 3,469,317 A | 9/1969 | Jarby | |
| 3,868,447 A | 2/1975 | Kliment | |
| 4,240,832 A | 12/1980 | Jandourek | |
| 4,308,062 A | 12/1981 | Cheung et al. | |
| 4,396,378 A | 8/1983 | Orlowski et al. | |
| 4,748,198 A | 5/1988 | Takahashi et al. | |
| 5,213,615 A | 5/1993 | Michl | |
| 5,330,746 A | 7/1994 | Friedman et al. | |
| 5,558,701 A | 9/1996 | Patel | |
| 5,708,052 A | 1/1998 | Fischer et al. | |
| 2007/0105975 A1* | 5/2007 | Orlowski et al. ........... 523/115 |

FOREIGN PATENT DOCUMENTS

| | | |
|---|---|---|
| DE | 19722596 A1 | 11/1967 |
| DE | 19722596 | 12/1998 |
| JP | 2001288025 | 10/2001 |

OTHER PUBLICATIONS

Search Report from corresponding British application dated Nov. 16, 2005.
Encyclopedia of Polymeric Science and Technology, vol. 10, 1969, pp. 597-615.
Search Report from corresponding British application dated Nov. 16, 2005.

* cited by examiner

*Primary Examiner*—Tae H Yoon
(74) *Attorney, Agent, or Firm*—Knobbe, Martens, Olson & Bear, LLP

(57) ABSTRACT

Disclosed are dental varnishes comprising reaction products of rosins with polyalcohols dissolved in mixtures of $C_2$-$C_4$ alcohols with $C_5$-$C_7$ hydrocarbons which have been found effective in preventing tooth decay and alleviating tooth sensitivity. Such varnishes may, optionally, incorporate therapeutic, antimicrobial and sensory enhancing ingredients.

18 Claims, No Drawings

CARIES PREVENTIVE DESENSITIZING AND FLUORIDIZING DENTAL VARNISHES

FIELD OF THE INVENTION

This invention relates to dental varnishes, more specifically varnishes comprising a resin and a solvent as are used to seal teeth.

BACKGROUND OF THE INVENTION

The oldest type of dental varnishes comprised solutions of copal resin, a fossilized plant-derived mined material, in chlorinated hydrocarbons and later in alcohols. These varnishes were almost exclusively used as coatings over the cavity walls prior to placement of amalgam-type restoratives. They were not suitable for use under the novel resin based restoratives because copal resin acts as an inhibitor of the polymerization process, negatively influencing the cure of the restorative material and, in consequence, the quality of the restoration. Incomplete cure of the material could also cause postoperative discomfort and, in case of vital teeth, serious damage to the pulp. Copal varnishes, although generally beneficial in preventing marginal leakage of new restorations, did not offer benefits of tooth fluoridation and, therefore, did not provide an important, additional measure of protection against secondary dental tissue decays.

Copal resin based varnishes were followed by varnishes based primarily on polyamide-type polymers, representing reaction products of aliphatic diamines with long chain carboxylic acids. Examples of such varnishes are described in U.S. Pat. No. 4,396,378. Synthetic varnishes generally do not inhibit the polymerization process of resin based restorative materials and, therefore, were suitable for use under amalgam as well as under polymeric restoratives. Because of their light consistency and low viscosity, they were unable to maintain fluoride salts in suspension. Their role was, therefore, limited to sealing dentin tubulae without providing the benefits of fluoridizing potentially vulnerable tooth surfaces.

Another type of dental varnish encompasses formulations comprising, in addition to film formers (natural or synthetic resin), therapeutic agents, to effect desirable changes in the chemistry of teeth, reduce tooth sensitivity and to protect vulnerable oral tissues against potentially damaging side effects resulting from contact with dental materials.

The most common among therapeutic additives in modern dental varnishes are fluoride salts, particularly sodium fluoride. The most commonly known fluoride containing dental varnishes are those comprising colophony resins as a film former, ethyl alcohol as a medium/solvent and sodium fluoride as the main, or only, therapeutic agent. Colophony is a natural resin derived from living trees and, as such, its characteristics frequently vary from one lot of resin to another. The differences often include properties relevant for the performance or esthetics of the varnish made with such resins. A desirable consistency of the varnish is important to achieve proper film thickness of the coating, to facilitate handling and, most of all, to prevent sedimentation of fluoride salts and other dispersed components of the formulation. Other disadvantages of these varnishes include their slow solvent release, resulting in a slow cure, and their unpleasant taste.

SUMMARY OF THE INVENTION

In accordance with one embodiment, there is provided a dental varnish for preventing or alleviating tooth sensitivity and/or reducing incidences of decay, wherein the varnish comprises a film-forming resin or resin mixture and a solvent, preferably comprising at least one $C_2$-$C_4$ aliphatic alcohol and at least one $C_5$-$C_7$ hydrocarbon. The resin mixture preferably comprises natural rosin, acid-modified rosin, partially polymerized rosin and combinations thereof. Preferably at least one rosin is an esterified rosin. In a preferred embodiment, the rosin is esterified with one or more polyalcohols, such as glycerol or pentaerythritol. In one embodiment, the solvent comprises an azeotropic or near azeotropic mixture of solvents, including, but not limited to, ethyl alcohol and n-hexane.

DETAILED DESCRIPTION OF THE PREFERRED EMBODIMENT

The subject of this invention is a new type of dental varnish, which while preserving all the advantages and functions of the prior art materials, fully eliminates their shortcomings.

Among the resin/film former components in the formulations disclosed herein are the esters of rosin with polyalcohols, including those with glycerol and pentaerythritol. Rosin, a plant-derived natural product, is a common ingredient in many dental products, particularly temporary cements and filling restorative materials. Chemical processing of rosin by its esterification results in a product of desirable and consistent characteristics. It was unexpectedly found that some of such esters dissolve in $C_2$-$C_4$ alcohols, and even better, in their mixtures with $C_5$-$C_7$ hydrocarbons.

In one embodiment, the solvent component comprising a mixture of alcohol and hydrocarbon, are azeotropic or near azeotropic mixtures. Solutions of rosin esters in such mixtures resulted in fast curing, non-irritating varnishes. The mixtures of alcohols and hydrocarbons shown in the table below are among those azeotropic or near azeotropic mixtures that are suitable in formulating varnishes. The relative weights given in the table relate only to the azeotropic mixtures at the given boiling points, and are not intended to restrict the absolute or relative amounts of alcohol and hydrocarbon in the varnish formulations. Varnish formulations may include solvent mixtures using the solvents and solvent combinations listed below, and other solvents, that are not in azeotropic or near-azeotropic mixtures. In a preferred embodiment, the solvent mixture used in a varnish has a boiling point below about 100° C.

TABLE 1

EXAMPLES OF ALCOHOLS/HYDROCARBON AZEOTROPIC MIXTURES

| Alcohol | Hydrocarbon Co-Solvent | Percentage (w/w) Alcohol | Azeotropic Boiling Point (° C.) |
|---|---|---|---|
| Isopropyl Alcohol | Isopentane | 5 | 27.8 |
| | n-Pentane | 6 | 35.5 |
| | n-Hexane | 23 | 62.7 |
| | Cyclohexene | 37 | 70.5 |
| | Cyclohexane | 33 | 68.6 |
| | n-Heptane | 50.5 | 76.4 |
| | Methyl Cyclohexane | 47.5 | 77.4 |
| | 2,5-Dimethylhexane | 62 | 79.0 |

TABLE 1-continued

EXAMPLES OF ALCOHOLS/HYDROCARBON AZEOTROPIC MIXTURES

| Alcohol | Hydrocarbon Co-Solvent | Percentage (w/w) Alcohol | Azeotropic Boiling Point (° C.) |
|---|---|---|---|
| n-Propyl Alcohol | n-Hexane | 4 | 65.6 |
| | Cyclohexane | 20 | 74.3 |
| | n-Heptane | 38 | 84.8 |
| Ethyl Alcohol | n-Pentane | 5 | 34.3 |
| | n-Hexane | 21 | 58.7 |
| | Cyclohexane | 30 | 64.9 |
| | n-Heptane | 49 | 70.9 |
| n-Butyl Alcohol | Cyclohexene | 5 | 82.0 |
| | Cyclohexane | 4 | 79.8 |
| | Methyl Cyclohexane | 21 | 96.4 |
| | 1-Heptene | 13 | 90.0 |
| | n-Heptane | 18 | 94.4 |
| Isobutyl Alcohol | n-Hexane | 2.5 | 68.3 |
| | Cyclohexene | 14.2 | 80.5 |
| | Cyclohexane | 14 | 78.1 |
| | Methyl Cyclohexane | 30 | 93.2 |
| | n-Heptane | 27 | 90.8 |
| sec-Butyl Alcohol | n-Hexane | 8 | 67.2 |
| | Cyclohexene | 18 | 76.0 |
| | Cyclohexane | 21 | 78.7 |
| | n-Heptane | 38 | 89.0 |

Esterified rosins are available, unlike colophony, in highly desirable, light colors, enabling the production of varnishes virtually invisible after their placement on the teeth—a highly desirable feature in certain clinical applications.

Rosin esters, and especially those using glycerol and pentaerythritol as esterfiying alcohols, allow for formulating desirable viscosity solutions at a concentration of 20%-75% by volume in the completed formulation. Such formulations feature fast solvent release combined with good mechanical characteristics of the coating. It was also found that the fluoride release (leaching) from such films is excellent and substantially better than that of prior art colophony varnishes.

In preferred embodiments, the varnishes comprise a film forming resin or mixture of resins in a solvent system. Preferred film forming resins include natural rosin, acid-modified rosin, partially polymerized rosin and combinations thereof. Part or all of the rosin may be esterified with an alcohol, preferably a polyalcohol such as glycerol, pentaerythritol and/or alkylene glycols. Preferred varnishes comprise at least about 20% rosin by weight, including about 30%, about 35%, about 40%, about 45%, about 50%, about 55%, about 60%, about 65%, about 70%, and about 75%, and also including percentages between these recited percentages, as well as ranges bordered on each end by recited percentages, such as about 30-70%. In one embodiment, the resin mixtures includes one or more other natural or artificial resins, including but not limited to, colophony, cumarone, copal, and polyamide resins. Such other resins are preferably present at about 1-20%, including about 5%, about 10% and about 15%, including percentages between these recited percentages, as well as ranges bordered on each end by recited percentages. Preferred polyamides include those which are a reaction product of aliphatic diamines with fatty acids.

Preferred solvent systems comprise an alcohol and a hydrocarbon. In one preferred embodiment, the solvent system comprises azeotropic or near-azeotropic mixtures of these components. Preferred alcohols for use in a solvent system include $C_2$-$C_4$ alcohols, including $C_3$ alcohols, wherein said alcohols may be linear, branched and/or cyclic. Preferred alcohols include ethyl alcohol, propyl alcohol (including its isomers n-propyl alcohol and isopropyl alcohol), butyl alcohol (including its isomers, namely n-butyl alcohol, sec-butyl alcohol, iso-butyl alcohol, and t-butyl alcohol), and blends thereof.

Preferred hydrocarbons include $C_5$-$C_7$ hydrocarbons, including $C_6$ hydrocarbon compounds, wherein said hydrocarbons may be linear, branched and/or cyclic, and may be alkanes and/or alkenes. The hydrocarbon component may comprise a single hydrocarbon or a blend of two or more hydrocarbons. Specific preferred hydrocarbons include isopentane. n-pentane, n-hexane, isohexanes, cyclohexene, cyclohexane, methylcyclopentane, n-heptane, methyl cyclohexane, 2,5-dimethylhexane, cyclohexene, methyl cyclohexene, 1-heptene, and mixtures thereof. The solvent mixture may include hydrocarbons outside the $C_5$-$C_7$ range.

In a preferred embodiment, the varnish comprises at least about 15% solvent by weight, including about 18%, about 19%, about 20%, about 21%, about 22%, about 23%, about 24%, about 25%, about 30%, and about 35%, and also including percentages between these recited percentages, as well as ranges bordered on each end by recited percentages. In a preferred embodiment, the varnish comprises at least about 4% alcohol component by weight, including about 5%, about 6% about 7%, about 8%, about 9%, about 10%, about 11%, about 12%, about 13%, and about 14%, also including percentages between these recited percentages, as well as ranges bordered on each end by recited percentages. In a preferred embodiment, the varnish comprises at least about 10% hydrocarbon component by weight, including about 11%, about 12% about 13%, about 14%, about 15%, about 16%, about 17%, about 18%, about 19% and about 20%, also including percentages between these recited percentages, as well as ranges bordered on each end by recited percentages. Certain embodiments of the invention may include components present at concentrations above and below the concentrations recited.

The varnish formulations optionally comprise a fluoridizing agent. Preferred fluoridizing agents include sodium fluoride, stannous fluoride, sodium monofluorophosphate, zinc hexafluorosilicate, and sodium hexafluorosilicate. When present, there is preferably about 0.1-10% fluoridizing agent by weight, including at least about 1%, about 2%, about 2.5%, about 3%, about 3.5% about 4%, about 4.5%, about 5%, about 5.5%, and about 6%, also including percentages between these recited percentages, as well as ranges bordered on each end by recited percentages, such as about 2.5%-6% and about 3-5%.

The varnish formulations optionally comprise one or more of the following: sweeteners, such as xylitol, sorbitol, aspartame, sodium saccharin, and mixtures thereof; flavorings such as peppermint oil, cherry, citric acid, orange, strawberry, vanilla, coconut, bubble gum flavors and mixtures thereof; coloring agents; and organic and/or inorganic fillers or thickeners. When a sweetener is present, it is preferably present at about 0.5-3% by weight, including about 1%, 1.5%, 2%, and 2.5% by weight, or some other quantity sufficient to impart an improved palatability to the varnish. When flavorings are present, they are preferably present at about 1-4% by weight, including about 1.5-3%, including about 2% and about 2.5% and values therebetween. When a filler or thickener is present, such as silica, it is preferably present at about 2-5%, including about 3-4% by weight.

The varnishes described herein may be applied to teeth using a suitable applicator, as is well-understood by those skilled in the art. Methods of using the varnish to seal a tooth include applying the varnish to a tooth and allowing the solvent to evaporate to leave behind a film which seals the tooth.

The invention is further described in the examples which are given solely for the purpose of illustration, and are not intended to limit its scope as defined in the patent claims. Unless stated otherwise, all percentages given below, and elsewhere herein, are by weight.

EXAMPLES OF FORMULATIONS AND PROPERTIES OF THE CEMENTS OF THIS INVENTION

Example 1

The varnish formulation consisted of:

| | |
|---|---|
| Pentaerythritol rosin ester | 68% |
| Silica | 3.5% |
| Xylitol | 2.7% |
| Bubble Gum Flavor | 3.0% |
| Sodium Fluoride | 4.2% |
| Ethyl alcohol | 5.8% |
| n-Hexane | 12.8% |

The formulation has shown an adequate ability to maintain sodium fluoride and xylitol in suspension. Curing time at 37° C. was approximately five minutes. Fluoride leachability from the cured varnish was demonstrated.

Example 2

The varnish formulation consisted of:

| | |
|---|---|
| Glycerol rosin ester | 60% |
| Polyamide (condensation product of ethylenediamine with fatty acids) | 5% |
| Silica | 4% |
| Aspartame | 0.5% |
| Peppermint Oil | 2% |
| Sodium Fluoride | 4.5% |
| Ethyl alcohol | 5.4% |
| n-Hexane | 18.6% |

The properties and performance of this formulation were substantially similar to this of Example 1.

Example 3

The varnish formulation consisted of:

| | |
|---|---|
| Glycerol rosin ester | 68% |
| Partially polymerized rosin | 6% |
| Sodium Saccharin Blend | 0.6% |
| Xylitol | 1.4% |
| Cherry flavor | 2% |
| Stannous Fluoride | 3.0% |
| Isopropyl alcohol | 5% |
| A blend of n-Hexane (85%) and 2-methyl pentane (15%) | 14% |

The properties and performance of this formulation were substantially similar to this of Example 1. The curing time, however, was approximately 25% longer.

Example 4

The varnish formulation consisted of:

| | |
|---|---|
| Glycerol rosin ester | 30% |
| Pentaerythritol rosin | 30% |
| Copal resin | 5% |
| Xylitol | 2.5% |
| Wild Cherry flavor | 2.5% |
| Sodium Monofluorophosphate | 5% |
| Ethyl alcohol | 12.5% |
| n-Heptane | 12.5% |

The properties and performance of this formulation were generally similar to those of Example 1. The curing time, however, was approximately 30% slower.

Example 5

The varnish formulation consisted of:

| | |
|---|---|
| Glycerol rosin ester | 64% |
| Silica | 3.2% |
| Xylitol | 2.3% |
| Wild Cherry flavor | 1.5% |
| Sodium Fluoride | 3.8% |
| Isopropyl alcohol | 8.3% |
| Cyclohexane | 16.6% |

The properties and performance of this formulation were generally similar to those of Example 1. The curing time at 37° C. was approximately 20 minutes.

What is claimed is:

1. Dental varnish for preventing or alleviating tooth sensitivity and/or reducing incidences of decay comprising:
    an esterified rosin, and
        a solvent comprising at least one $C_2$-$C_4$ aliphatic alcohol and at least one $C_5$-$C_7$ hydrocarbon.

2. A varnish of claim 1, wherein said rosin is esterified with one or more polyalcohols.

3. The varnish of claim 1, wherein said rosin is esterified with glycerol.

4. The varnish of claim 1, wherein said rosin is esterified with pentaerythritol.

5. The varnish of claim 1, wherein said esterified rosin is present in a mixture with non-modified rosin, partially polymerized rosin, and/or acid-modified rosin.

6. The varnish of claim 1, wherein said solvent comprises an azeotropic or near azeotropic mixture of ethyl alcohol with n-hexane, its isomers or mixtures thereof.

7. The varnish of claim 1, wherein said solvent comprises an azeotropic or near azeotropic mixture of isopropyl or propyl alcohol with n-hexane, its isomers or mixtures thereof.

8. The varnish of claim 1 containing 0.1%-10% of fluoride salt selected from the group consisting of sodium fluoride, potassium fluoride, sodium monofluorophosphate, stannous fluoride, zinc hexafluorosilicate, sodium hexafluorosilicate and potassium hexafluorosilicate.

9. The varnish of claim 1, wherein said rosin component is present at a concentration of 20%-75% by weight.

10. The varnish of claim 1, wherein said solvent has a boiling point at atmospheric pressure below 100° C.

11. The varnish of claim 1 additionally containing coloring agents.

12. The varnish of claim 1 additionally containing sweeteners and/or flavorings.

13. The varnish of claim 1 additionally containing inorganic and/or organic fillers.

14. The varnish of claim 13, wherein said inorganic filler is silica.

15. The varnish of claim 1 additionally containing 1%-20% of other natural or synthetic resin.

16. The varnish of claim 15, wherein said resin comprises colophony, copal and/or cumarone resin.

17. The varnish of claim 15, wherein said resin comprises a polyamide.

18. The varnish of claim 17, wherein said polyamide is a reaction product of aliphatic diamines with fatty acids.

* * * * *